United States Patent
Bignazzi et al.

(10) Patent No.: US 6,737,558 B2
(45) Date of Patent: May 18, 2004

(54) PROCESS FOR THE SEPARATION OF 2,6-DIMETHYLNAPHTHALENE FROM MIXTURES CONTAINING IT

(75) Inventors: Renzo Bignazzi, Legnano (IT); Gianni Pandolfi, Novara (IT)

(73) Assignees: ENICHEM S.p.A., San Donato Milanese (IT); ENI S.p.A., Rome (IT)

(*) Notice: Subject to any disclaimer, the term of this patent is extended or adjusted under 35 U.S.C. 154(b) by 0 days.

(21) Appl. No.: 09/851,131

(22) Filed: May 9, 2001

(65) Prior Publication Data

US 2002/0023318 A1 Feb. 28, 2002

(30) Foreign Application Priority Data

May 10, 2000 (IT) .......................... MI2000A1025

(51) Int. Cl.⁷ .................................. C07C 7/14
(52) U.S. Cl. ................. 585/812; 585/814; 585/816; 585/817
(58) Field of Search ................. 585/812, 814, 585/816, 817

(56) References Cited

U.S. PATENT DOCUMENTS 3,957,896 A * 5/1976 Yokoyama et al. ......... 585/479
6,057,487 A * 5/2000 Munson et al. ............. 585/814

FOREIGN PATENT DOCUMENTS

EP 0 792 858 9/1997

* cited by examiner

*Primary Examiner*—Walter D. Griffin
*Assistant Examiner*—Tam M. Nguyen
(74) *Attorney, Agent, or Firm*—Oblon, Spivak, McClelland, Maier & Neustadt, P.C.

(57) ABSTRACT

Process for the separation of 2,6-dimethylnaphthalene from mixtures containing it, comprising the following operations:

crystallization by the addition of a solvent and cooling of the mixture to a temperature higher than the formation value of the first eutectic;

removal of the mother liquor by repeated washings;

dissolution of the solid obtained;

crystallization by cooling;

filtration.

4 Claims, No Drawings

PROCESS FOR THE SEPARATION OF 2,6-DIMETHYLNAPHTHALENE FROM MIXTURES CONTAINING IT

The present invention relates to a process which, on the basis of suitable crystallization and filtration techniques, allows the separation of 2,6-dimethylnaphthalene (hereunder, also 2,6 DMN) from mixtures in which it is present in a concentration higher than the eutectic ratios with the other isomers.

2,6-dimethylnaphthalene is an interesting intermediate for the preparation of 2,6-naphthalenedicarboxylic acid which, in turn, is a very valuable monomer for the preparation of high performance polymeric materials.

It is known that industrial processes for the production of 2,6-dimethylnaphthalene are substantially based on the recovery of this compound from fractions deriving from the reforming of kerosene or from FCC oil fractions. In the former case, the dimethylnaphthalenes must be separated by distillation and subsequently a large part of the 2,6 isomer is isolated by means of selective absorptions and/or crystallizations. In the latter case, there is an additional problem due to the presence of nitrogen and sulfur which poison the catalysts used for the separation and/or isomerization phases.

A synthesis process is also known (U.S. Pat. Nos. 4,990,717; 5,118,892; 5,073,670; 5,030,781; 5,012,024) which, by means of a series of alkenylation, cyclization, dehydrogenation and isomerization processes, leads to the selective preparation of 2,6-dimethylnaphthalene: the first step involves starting from o-xylene and 1,3-butadiene. Alkylation on the part of butadiene takes place, in the presence of a basic catalyst, on one of the methyl groups of o-xylene, with the formation of 5-(o-tolyl)2-pentene. The latter is separated and, in the presence of a zeolitic catalyst (type Y) containing Pt and Cu, is subjected to an internal cyclization reaction. 1,5-dimethyltetraline is thus obtained, which is subsequently dehydrogenated with the help of a Pt/Re catalyst supported on alumina. This is followed by a separation phase to isolate the 1,5-dimethylnaphthalene, which is then isomerized to 2,6 with another zeolitic catalyst.

As can be seen, there are various passages in this synthesis method. This is a problem from an economic point of view. Furthermore with every passage (chemical reaction) there are secondary reactions and consequently separations to guarantee the purity of the intermediates or end-product. The use in the process in question of a basic catalyst containing Na and K, as such or supported, creates problems relating to handling and safety.

Other methods for the synthesis of 2,6-dimethylnaphthalene are equally known, starting from different naphthalene raw materials (for example, according to the U.S. Pat. No. 5,043,501, or European patent applications 950,650 or the co-pending Italian patent application 99/A 001533 also in the name of same Applicant), and fundamentally based on alkylation and/or isomerization reactions which, however, cause the formation, even after normal separation operations, of mixtures in which 2,6-dimethylnaphthalene is at least present with other dimethylnaphthalene isomers even if, with reference to the catalyst used, or raw materials used, this co-presence can also be reduced within acceptable limits.

The Applicant has now found, and this forms the object of the present invention, a process which, by means of a suitable combination of crystallization and filtration techniques, enables the production of high purity 2,6-dimethylnaphthalene, by separation from the mixtures containing it, no matter what preparation process is used and when the 2,6-dimethylnaphthalene is present in the mixture of interest in a concentration higher than the eutectic ratios with the other isomers.

It is normally known that on cooling a mixture having the above composition, the first product which begins to crystallize is the 2,6-dimethylnaphthalene isomer and that, to prevent other products from crystallizing, it is advisable not to lower the temperature below the value at which, with the compositions of the mixture, the crystallization of a eutectic, consisting of different dimethylnaphthalenes, initiates.

There are two phenomena which complicate the separation of high purity 2,6 DMN:

The crystal obtained by crystallization from the molten state has such a morphology that, after separation of the mother liquor by filtration, the residual wetting of the solid is high and therefore the titer of 2,6 DMN in the solid is low.

In the crystallization of 2,6 DMN from isomeric mixtures there is the presence of a co-crystallization phenomenon and therefore, even when operating above the formation temperature of eutectics, there is the presence of other compounds in the solid, which prevent the pure 2,6 DMN from separating even after the complete removal of the wetting liquid. In particular, 2,7 DMN co-crystallizes (2,7/2,6 in the solid=about 10%•2,7/2,6 in the mother liquor).

According to the state of the art, it seems possible to eliminate the wetting of the solid by washing; the use of a solvent however can cause the risk of high losses of solid by dissolution.

The most delicate and difficult aspect to be solved is co-crystallization: an equilibrium in fact is established between solid and mother liquor and consequently a part of the compound is adsorbed in the solid, co-crystallizes and therefore reduces the purity of the crystalline solid.

This type of impurity cannot obviously be reduced by washings which only serve to improve the separation between the solid and its mother liquor.

Various literature, also relating to patents, describes methods for the crystallization of 2,6 DMN using different techniques: the main ones involve the complexing of 2,6 DMN before crystallizing it, or its crystallization at high pressure.

These are basically solutions which, although theoretically interesting, are not easy to produce, at least from the point of view of industrial practice. Furthermore they allow either high purities or high recovery yields to be obtained: for example, U.S. Pat. No. 6,018,086 describes a purification process in which a purity of 2,6 DMN of 87% is reached, with a recovery of 2,6 DMN of 68%; U.S. Pat. No. 6,018,087 on the other hand, describes a purification process in which a purity of 2,6 DMN >99% is obtained with a recovery of 2,6 DMN of 14.5%.

The process according to the present invention, which is surprisingly simple and effective, can, on the contrary, be easily transferred to larger and more committing scales than merely experimental levels and allows the production of 2,6-dimethylnaphthalene having a very high degree of purity, with contemporary recoveries close to the theoretical value, without any of the limits and disadvantages which characterize the methods described in the state of the art.

The process according to the present invention basically comprises the following operations:

Crystallization of 2,6-dimethylnaphthalene by addition to the mixture containing it of a solvent and cooling the mixture thus obtained to a temperature higher than the formation value of the first eutectic;

Repeated washings with a solvent to remove the wetting mother liquor;

Dissolution of the solid obtained in the previous crystallization phase;

Recrystallization of the 2,6-dimethylnaphthalene by cooling;

Filtration of the solid obtained.

The solvent, when used according to the necessities of the above operations, can always be the same, or different solvents can be used, these however being selected from low molecular weight aliphatic alcohols and/or glycols: it is naturally advantageous and preferable to use the same solvent for the whole duration of the process and, among all possible alcohols, the use of methanol is preferably recommended.

Without entering into the interaction mechanisms of the various operations, these can be better illustrated as follows:

In the first phase, the use of a crystallization solvent improves the morphology of the crystal and therefore facilitates its separation from the mother liquor; in addition, the use as solvent of an aliphatic alcohol surprisingly reduces the co-crystallization degree and consequently the isomers present as solid in the 2,6 DMN crystal (2,7/2,6 in the solid=about 2%•2,7/2,6 in the mother liquor).

In a second phase, it is preferable to remove the wetting of the crystal with washing operations with a solvent. It has been observed that low molecular weight aliphatic alcohols have the appropriate characteristics for being used for this purpose. Although these substances, in fact, mix with molten DMN, they have a low solvent capacity with respect to these solids (in particular with respect to 2,6 DMN).

In a third and final phase the washed solid can be further purified by dissolution and re-crystallization from a solvent. In this case the use of an aliphatic alcohol allows complete control of the co-crystallization phenomenon and this fact, together with the morphology of the crystal, which enables easy separation from the mother liquor by filtration, allows the highest purity of 2,6 DMN to be obtained.

In short, when operating as described above, the maximum purity is obtained, even in the presence of isomers creating co-crystallization phenomena, together with high recovery yields, by exploiting the low solubility of 2,6 DMN in the solvent selected.

The residual "solvent" present in the solid as wetting liquid, can be removed by evaporation by heating it to a temperature higher than the boiling point of the "solvent".

With respect to the known procedures for the separation of 2,6-dimethylnaphthalene from mixtures containing it, the process according to the present invention has the following evident advantages:

High titer of 2,6 DMN separated also in the presence of high concentrations of isomers which produce co-crystallization phenomena.

High recovery, practically equal to the theoretical value, with respect to the limits due to the formation of eutectics.

Simplicity of the method, a sequence of three simple operations effected with limited thermal ranges, close to room temperature and at a pressure equal to or close to atmospheric pressure.

The use of a single "solvent" in the three different phases which allows the washing liquid in the initial crystallization to be re-used (either partially or completely) and the mother liquor recovered from the re-crystallization for the washings, to be recycled.

In the case of the use of methanol as solvent, a further advantage consists in the possibility of recycling the mother liquor of the first crystallization to the upstream alkylation section which produces the mixture of DMN isomers (for example, according to the procedure described in Italian patent application MI98A 00809 of Apr. 17, 1998 filed by the same applicant).

The addition of the solvent to the mixture of isomers in crystallization modifies the co-crystallization equilibrium, significantly reducing this phenomenon and in particular the co-crystallization of 2,7 DMN which drops from 10% to about 2%.

Another important advantage of the use of the solvent as re-crystallization solvent is that it further reduces co-crystallization allowing the separation of high purity 2,6 DMN.

An additional advantage consists in the low solubility of 2,6 DMN in the solvent which reduces product losses of the whole cycle to the minimum and allows the two crystallizations to be effected at temperatures slightly lower than those without the use of a solvent.

EXAMPLE

Crystallization and Filtration

3 Kg of a mixture of DMN (27.6% 2,6 DMN; 15.9% 2,7 DMN; 27.4% 1,6 DMN; 29.1% others) and 0.75 Kg of methanol are charged into a 5 liter stirred reactor, equipped with a jacket.

After being melted at 55° C., the mixture is cooled to 41° C. to activate the crystallization of 2,6 DMN and is brought to 46° C. to start the crystallization, in the presence of a few crystals of 2,6 DMN, establishing a temperature profile decreasing to 25° C. over a period of about 6 hours.

The temperature of 25° C. was selected to prevent other isomers, in particular 2,7 DMN, from starting to crystallize.

The reactor is emptied by filtering the suspension in a G2 porous filter, separating the mother liquor (2.79 Kg) from the solid panel (0.96 Kg) containing a wetting liquid having the same composition as the mother liquor.

Upon quantitatively distinguishing the solid from the wetting liquid, the following is observed:

in the solid the presence of about 98.8% of 2,6 DMN and about 1.2% of 2,7 DMN a ratio of 1 to 1.14 between the solid and wetting liquid.

The composition of the panel, referring only to DMN, proves to be 59.5% of 2,6 DMN; 9.31% of 2,7 DMN; 15.1% of 1,6 DMN; 16% of others.

The composition of the mother liquor, referring only to DMN, is: 15% of 2,6 DMN; 18.5% of 2,7 DMN; 32.2% of 1,6 DMN; 34.2% of others.

$1^{st}$ Washing

The panel of the previous phase (0.96 Kg) was washed with about 1.6 Kg of methanol at a temperature of about 20° C., separating the washing liquid (1.680 Kg) from the solid panel (0.880 Kg).

Upon quantitatively distinguishing the solid from the wetting liquid, the following is observed:

in the solid the presence of about 98.8% of 2,6 DMN and about 1.2% of 2,7 DMN a ratio of 1 to 0.96 between the solid and wetting liquid.

The composition of the panel, referring only to DMN, proves to be 86.0% of 2,6 DMN; 3.86% of 2,7 DMN; 4.93% of 1,6 DMN; 5.24% of others.

The composition of the washing liquid, referring only to DMN, is: 15.2% of 2,6 DMN; 18.5% of 2,7 DMN; 32.2% of 1,6 DMN; 34.2% of others.

2<sup>nd</sup> Washing

The panel of the previous phase (0.880 Kg) was washed with about 1.4 Kg of methanol at a temperature of about 20° C., separating the washing liquid (1.547 Kg) from the solid panel (0.733 Kg).

Upon quantitatively distinguishing the solid from the wetting liquid, the following is observed:

in the solid the presence of about 98.8% of 2,6 DMN and about 1.2% of 2,7 DMN a ratio of 1 to 0.69 between the solid and wetting liquid.

The composition of the panel, referring only to DMN, proves to be 96.3% of 2,6 DMN; 1.7% of 2,7 DMN; 0.94% of 1,6 DMN; 1.0% of others.

The composition of the washing liquid, referring only to DMN, is: 27.1% of 2,6 DMN; 16.0% of 2,7 DMN; 27.6% of 1,6 DMN; 29.3% of others.

Re-Crystallization

The panel (equal to 0.733 Kg) was dissolved under heat with about 4.9 Kg of methanol at a temperature of 64° C. under stirring, and was then left to cool under static conditions with a temperature profile decreasing to 20° C. over a period of about 3 hours.

The suspension obtained was filtered on a G2 porous septum, separating the mother liquor (5.230 Kg) from the solid panel (0.403 Kg) containing a wetting liquid having the same composition as the mother liquor (almost all methanol).

The composition of the panel, referring only to DMN, proves to be 99.8% of 2,6 DMN; 0.19% of 2,7 DMN; 0.005% of 1,6 DMN; 0.005% of others.

The composition of the mother liquor, referring only to DMN, is: 80.6% of 2,6 DMN; 8.64% of 2,7 DMN; 5.21% of 1,6 DMN; 5.54% of others.

Final Drying

The panel was charged into a flask evaporating the residual methanol at a temperature of about 90° C.

The final composition of the solid is 99.8% of 2,6 DMN; 0.19% of 2,7 DMN; 0.005% of 1,6 DMN; 0.005% of others.

The final quantity of 2,6 DMN crystal is 0.369 Kg with a 44.5% recovery.

The quantity of methanol distilled is 0.0336 Kg.

What is claimed is:

1. A process for the separation of 2,6-dimethylnaphthalene from a starting mixture containing it and isomers thereof comprising the following operations:

(A) crystallization of 2,6-dimethylnaphthalene by the addition of methanol and cooling of the mixture thus obtained to a temperature higher than the highest formation value of any eutectic of 2,6-dimethylnaphthalene and another isomer in the mixture, whereby a mother liquor containing solid, said solid comprising 2,6-dimethylnaphthalene, is produced;

(B) removal of the mother liquor by repeated washings with a solvent;

(C) dissolution in a solvent of the solid obtained, whereby a solution is produced;

(D) crystallization of said solution by cooling, whereby a suspension is produced;

(E) filtration of said suspension, whereby said 2,6-dimethylnaphthalene is separated.

2. The process for the separation of 2,6-dimethylnaphthalene according to claim 1, wherein the starting mixture contains 2,6-dimethylnaphthalene in a concentration higher than its eutectic concentration with isomers thereof that are present in said starting mixture.

3. The process for the separation of 2,6-dimethylnaphthalene according to claim 1, wherein said isomers include 2,7-dimethylnaphthalene.

4. The process for the separation of 2,6-dimethylnaphthalene according to claim 2, wherein said isomers include 2,7-dimethylnaphthalene.

* * * * *